(12) United States Patent
Rezach et al.

(10) Patent No.: US 11,229,462 B2
(45) Date of Patent: Jan. 25, 2022

(54) HEAD ASSEMBLY INSERTERS

(71) Applicant: Warsaw Orthopedic, Inc., Warsaw, IN (US)

(72) Inventors: William A. Rezach, Covington, TN (US); Jason M. May, St. Johns, FL (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 349 days.

(21) Appl. No.: 16/405,636

(22) Filed: May 7, 2019

(65) Prior Publication Data

US 2020/0352612 A1 Nov. 12, 2020

(51) Int. Cl.
*A61B 17/70* (2006.01)
*A61F 2/46* (2006.01)

(52) U.S. Cl.
CPC ........ *A61B 17/7076* (2013.01); *A61F 2/4611* (2013.01); *A61B 17/7032* (2013.01); *A61F 2/4603* (2013.01); *A61F 2002/4627* (2013.01)

(58) Field of Classification Search
CPC .......................... A61B 17/7076; A61B 17/7035
See application file for complete search history.

(56) References Cited

U.S. PATENT DOCUMENTS

| | | | |
|---|---|---|---|
| 6,440,133 B1 * | 8/2002 | Beale | A61B 17/7032 606/104 |
| 7,575,581 B2 | 8/2009 | Lovell | |
| 7,854,751 B2 | 12/2010 | Sicvol et al. | |
| 7,988,699 B2 | 8/2011 | Martz et al. | |
| 8,303,602 B2 | 11/2012 | Biedermann et al. | |
| 8,313,516 B2 * | 11/2012 | Konieczynski | A61B 17/8605 606/266 |
| 8,608,746 B2 | 12/2013 | Kolb et al. | |
| 8,876,869 B1 | 11/2014 | Schafer et al. | |
| 9,084,642 B2 | 7/2015 | Peultier | |
| 9,149,308 B2 | 10/2015 | Biedermann et al. | |
| 9,326,798 B2 | 5/2016 | Kolb et al. | |
| 9,510,874 B2 | 12/2016 | Kruger | |
| 9,517,092 B2 | 12/2016 | Biedermann et al. | |
| 9,532,814 B2 | 1/2017 | Harper | |
| 9,572,605 B2 | 2/2017 | Shipp | |
| 9,615,862 B1 | 4/2017 | Doubler et al. | |
| 9,888,948 B2 | 2/2018 | Petit | |
| 9,968,385 B2 | 5/2018 | Biedermann | |

(Continued)

*Primary Examiner* — Andrew Yang
(74) *Attorney, Agent, or Firm* — Fox Rothschild LLP

(57) ABSTRACT

Systems, instruments, and methods for attaching a head assembly to a fastener are provided. The systems, instruments, and methods may include a surgical instrument. The surgical instrument may include an elongated first member; a first tubular member, in which a portion of the elongated first member is positioned within the first tubular member; a second tubular member, in which the portion of the elongated first member and a portion of the first tubular member are positioned within the second tubular member; and at least one grasping member, in which a portion of the at least one grasping member is pivotably coupled to the first tubular member and another portion of the at least one grasping member is pivotably coupled to the second tubular member. In one or more cases, the at least one grasping member may actuate translation of the first tubular member and the second tubular member.

22 Claims, 16 Drawing Sheets

(56) References Cited

U.S. PATENT DOCUMENTS

| | | |
|---|---|---|
| 10,058,359 B2 | 8/2018 | Black et al. |
| 10,123,826 B2 | 11/2018 | Harper |
| 10,219,837 B2 | 3/2019 | Jackson et al. |
| 2017/0296234 A1 | 10/2017 | Jackson et al. |
| 2017/0333085 A1 | 11/2017 | Jackson et al. |
| 2018/0325560 A1 | 11/2018 | Jackson et al. |

* cited by examiner

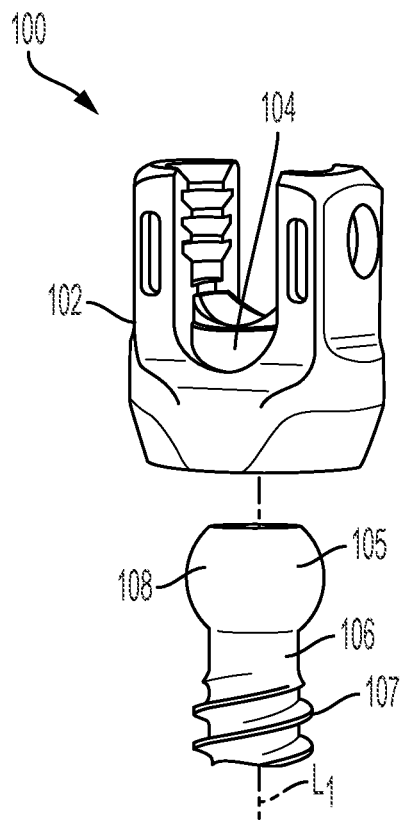
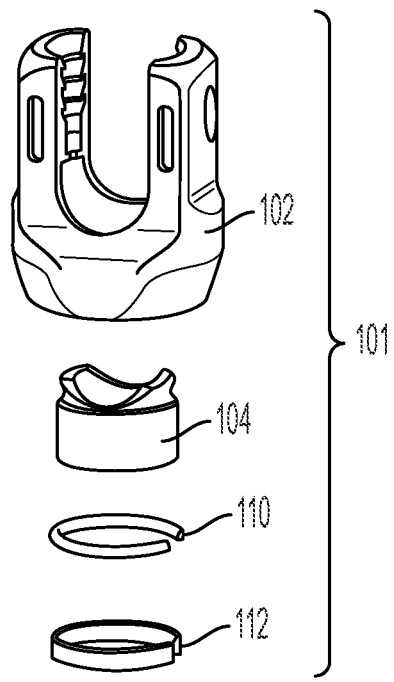
FIG. 1A
FIG. 1B
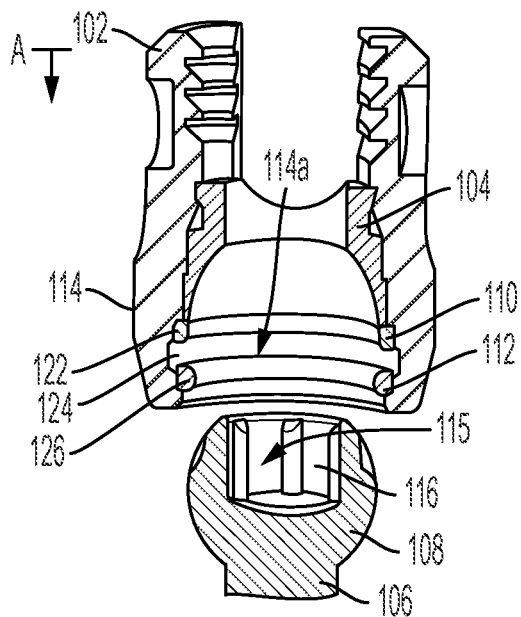
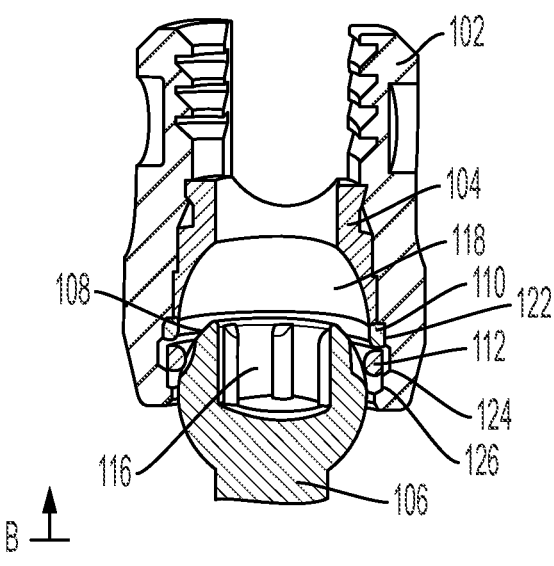
FIG. 1C
FIG. 1D

HEAD ASSEMBLY INSERTERS

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation, and exercise can be effective, however, may fail to relieve the symptoms associated with these disorders. Surgical treatment of these spinal disorders includes correction, fusion, fixation, discectomy, laminectomy, and/or implantable prosthetics. As part of these surgical treatments, spinal constructs, which include implants such as bone fasteners, connectors, plates, and vertebral rods are often used to provide stability to a treated region. These implants can redirect stresses away from a damaged or defective region while healing takes place to restore proper alignment and generally support the vertebral members. Surgical instruments are employed, for example, to engage the fasteners for attachment to two or more vertebral members. This disclosure describes improvements over these prior technologies.

SUMMARY

The present disclosure relates generally relates to medical devices for the treatment of musculoskeletal disorders, and more particularly to surgical systems and methods for treating a spine.

In one or more embodiments, the disclosed technology relates to a surgical instrument which may include an elongated first member. In one or more cases, the surgical instrument may include a first tubular member, in which a portion of the elongated first member is positioned within the first tubular member. In one or more cases, the surgical instrument may include a second tubular member, in which the portion of the elongated first member and a portion of the first tubular member are positioned within the second tubular member. In one or more cases, the surgical instrument may include at least one grasping member, in which a portion of the at least one grasping member is pivotably coupled to the first tubular member and another portion of the at least one grasping member is pivotably coupled to the second tubular member. In one or more cases, the at least one grasping member is configured to actuate translation of the first tubular member and the second tubular member. In one or more cases, the elongated first member is configured to translate within a portion of the first tubular member based on a position of the first tubular member with respect to the second tubular member.

In one or more embodiments, the disclosed technology relates to a modular surgical instrument which may include an elongated first member. In one or more cases, the modular surgical instrument may include an elongated second member having a first end and a second end disposed on an opposite side of the first end, in which the first end includes a working end attachment. In one or more cases, the modular surgical instrument may include at least grasping member. In one or more cases, the modular surgical instrument may include a first working end. In one or more cases, the first working end may include a first interlocking portion disposed on a proximal end of the first working end and configured to interlock with a second interlocking portion disposed on a proximal end of the working end attachment. In one or more cases, the first working end may include a first tubular member, in which a portion of the elongated first member is positioned within the first tubular member. In one or more cases, the first working end may include a second tubular member, in which the portion of the elongated first member and a portion of the first tubular member are positioned within the second tubular member. In one or more cases, a portion of the at least one grasping member is pivotably coupled to the first tubular member and another portion of the at least one grasping member is pivotably coupled to the first end of the elongated second member. In one or more cases, the first working end is removable coupled to the first end of the elongated second member, via the first interlocking portion and the second interlocking portion. In one or more cases, the at least one grasping member is configured to actuate translation of the first tubular member and the second tubular member.

In one or more embodiments, the disclosed technology relates to a surgical system which may include an implant. In one or more cases, the implant may include an assembly head and a fastener, in which the assembly head is configured to interlock with the fastener. In one or more embodiments, the disclosed technology relates to a surgical system which may include a surgical instrument. In one or more cases, the surgical instrument may include an elongated first member. In one or more cases, the surgical instrument may include a first tubular member, in which a portion of the elongated first member is positioned within the first tubular member. In one or more cases, the surgical instrument may include a second tubular member, in which the portion of the elongated first member and a portion of the first tubular member are positioned within the second tubular member. In one or more cases, the surgical instrument may include at least one grasping member. In one or more cases, a portion of the at least one grasping member is pivotably coupled to the first tubular member and another portion of the at least one grasping member is pivotably coupled to the second tubular member. In one or more cases, the at least one grasping member is configured to actuate translation of the first tubular member and the second tubular member. In one or more cases, the first tubular member is configured to interlock the assembly head and the fastener.

The foregoing and other objects, features and advantages of the invention will be apparent from the following more particular descriptions of exemplary embodiments of the invention as illustrated in the accompanying drawings wherein like reference numbers generally represent like parts of the disclosure.

BRIEF DESCRIPTION OF DRAWINGS

The following drawings are illustrative of particular embodiments of the present disclosure and therefore do not limit the scope of the present disclosure. The drawings are not to scale and are intended for use in conjunction with the explanations in the following detailed description.

FIG. 1A is a perspective view of an example implant in an unconnected state, according to one or more embodiments of the present disclosure.

FIG. 1B is a break away perspective view of a head assembly of the example implant shown in FIG. 1A, according to one or more embodiments of the present disclosure.

FIGS. 1C-1G are perspective views of connecting the example implant shown in FIG. 1A, according to one or more embodiments of the present disclosure.

DETAILED DESCRIPTION

Figure 1E:
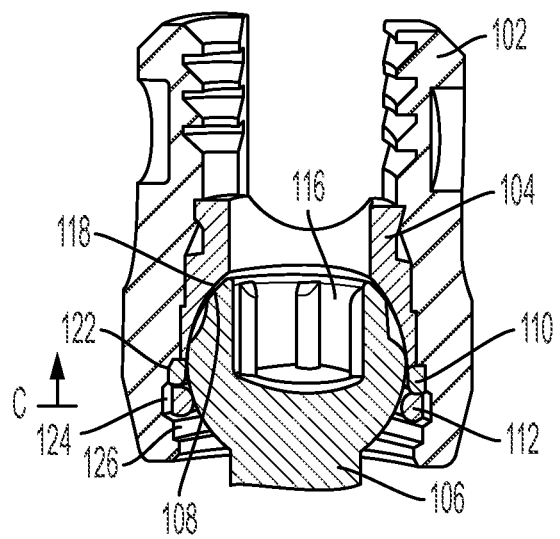

The following discussion omits or only briefly describes certain conventional features related to surgical systems for treating the spine, which are apparent to those skilled in the art. It is noted that various embodiments are described in detail with reference to the drawings, in which like reference numerals represent like parts and assemblies throughout the several views. Reference to various embodiments does not limit the scope of the claims appended hereto. Additionally, any examples set forth in this specification are intended to be non-limiting and merely set forth some of the many possible embodiments for the appended claims. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc. It must also be noted that, as used in the specification and the appended claims, the singular forms "a," "an" and "the" include plural referents unless otherwise specified, and that the terms "comprises" and/or "comprising," when used in this specification, specify the presence of stated features, elements, and/or components, but do not preclude the presence or addition of one or more other features, steps, operations, elements, components, and/or groups thereof.

Embodiments of the present disclosure relate generally, for example, to medical devices and methods for treating musculoskeletal disorders, and more particularly, to surgical systems and methods for treating the spine. Embodiments of the devices, methods, and systems are described below with reference to the Figures.

FIG. 1A is a perspective view of an example implant 100 in an unconnected state, according to one or more embodiments of the present disclosure. FIG. 1B is a break away perspective view of a head assembly 101 of the example implant 100 shown in FIG. 1A, according to one or more embodiments of the present disclosure.

In one or more embodiments, the implant 100 includes a fastener 106 and a head assembly 101. The fastener 106 includes an elongated shaft 107 configured for penetrating tissue and a head 108 configured to engage with the head assembly 101. The head 108 includes an outer circumferential surface 105 having a substantially uniform diameter thereabout. In some embodiments, all or only a portion of the surface 105 includes a spherical configuration. The head 108 includes an inner surface 116 that defines a cavity, such as, for example, a mating surface 115. The mating surface 115 is configured to receive an instrument and/or tool extension, such as, for example, a mating surface 211 on an end 213 of a plunger 212, as discussed herein. The mating surface 115 is centrally positioned with respect to head 108. The mating surface 115 may be coaxial with axis Li. In one or more cases, the mating surface 211 may mate with a lead-in chamfer and/or counter sink of the fastener 106.

The head assembly 101 may include a receiver 102 that houses a crown 104, an upper retainer 110, and a lower retainer 112 within the receiver base 114 of the receiver 102. The receiver base 114 may include a receiving portion 114a that defines a cavity within the receiver base 114. The receiving portion 114a may include an upper chamber 122, an expansion chamber 124, and a lower chamber 126. The upper chamber 122, the expansion chamber 124, and the lower chamber 126 may be positioned on top of one another, and each may extend circumferentially around the receiving portion 114a. The upper chamber 122 and the lower chamber 126 may be positioned on opposite sides of the expansion chamber 124. The upper chamber 122 and lower chamber 126 may each have a diameter smaller than the expansion chamber 124. In one or more cases, the upper chamber 122 is sized to receive the upper retainer 110 in a compressed state, the expansion chamber 124 is sized to fit the upper retainer 110 in an expanded state (i.e., a free state), and the lower chamber 126 is sized to receive the lower retainer 112 in an expanded state (i.e., a free state). In one or more cases, the expansion chamber 124 may be sized to receive at least a portion of the upper retainer 110 and at least a portion of the lower retainer 112. In one or more cases, the expansion chamber 124 is sized to house the upper retainer 110 and/or the lower retainer 112 in an expanded state.

In one or more cases, the upper retainer 110 and the lower retainer 112 may each be made from a resilient material, such as a stainless steel, cobalt chrome, or titanium alloy. The upper retainer 110 may be an open ring contracted during assembly within the receiver 114 and expanded when the crown 104 pushes the upper retainer 110 into the expansion chamber 124. The lower retainer 112 may be an open ring positioned within the receiver 114 in an expanded state. In one or more cases, the upper retainer 110 may be contracted to fit within the upper chamber 122. The upper retainer 110 may expand when positioned within the expansion chamber 124. The lower retainer 112 may expand around the head 108 of the fastener 106 when positioned within the expansion chamber 124.

Figure 1F:
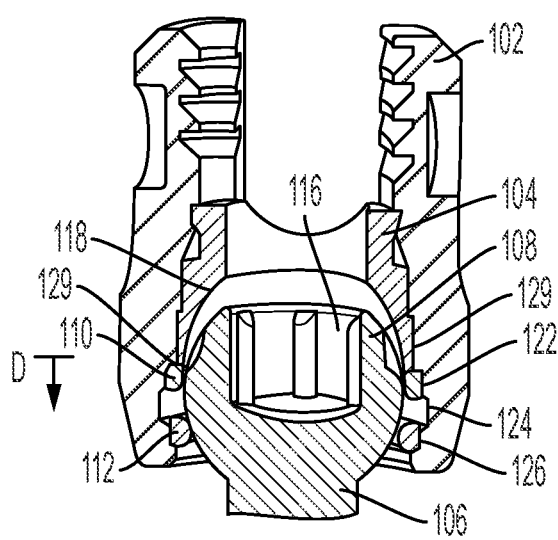
Figure 1G:
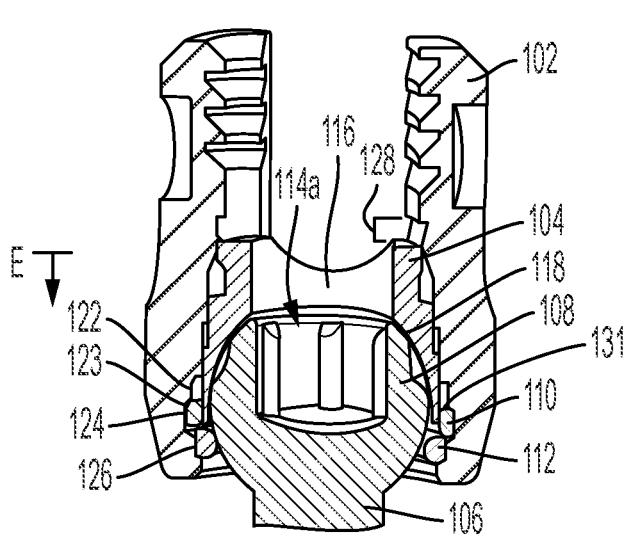
Figure 1H:
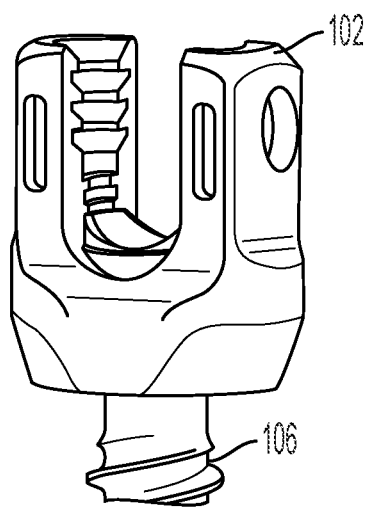
FIG. 1H is a perspective view of the head assembly connected to a fastener of the example implant, according to one or more embodiments of the present disclosure.

FIGS. 1C-1G are perspective views of connecting the example implant 100 shown in FIG. 1A, according to one or more embodiments of the present disclosure. FIG. 1H is a perspective view of the head assembly 101 connected to the fastener 106 of the example implant 100, according to one or more embodiments of the present disclosure.

To assemble the implant 100, the proximal end of the receiver 102 is inserted onto the head 108 of the fastener 106, as shown by the A direction in FIG. 1C. As the head 108 of the fastener 106 enters the receiving portion 114a, the surface 105 of the head 108 may contact the lower retainer 112 and move the lower retainer 112 into the expansion chamber 124, as shown by the B direction in FIG. 1D. In the expansion chamber 124, the lower retainer 112 expands to a size, such that the head 108 may pass though the inner diameter of the lower retainer 112.

Having expanded in size, the head 108 passes through the inner diameter of the lower retainer 112, in a direction C as shown in FIG. 1E. The proximal surface of the head 108 is pressed against the inner surface 118 of the crown 104, and the lower retainer 112 moves to a distal end of the head 108, in a direction D as shown in FIG. 1F. The crown 104 may be moved downwards in the receiving portion 114a, in which the bottom surface 129 of the crown 104 moves the upper retainer 110 out of the upper chamber 122 and into the expansion chamber 124. In the expansion chamber 124, the upper retainer 110 expands such that the upper surface 131 of the upper retainer 110 interfaces with the upper rim 123 of the expansion chamber 124. In this state, the lower retainer 112 may no longer enter into the expansion chamber 124, thereby locking the head assembly 101 onto the head 108 of the fastener 106, as shown in FIGS. 1G and 1H.

Figure 2A:
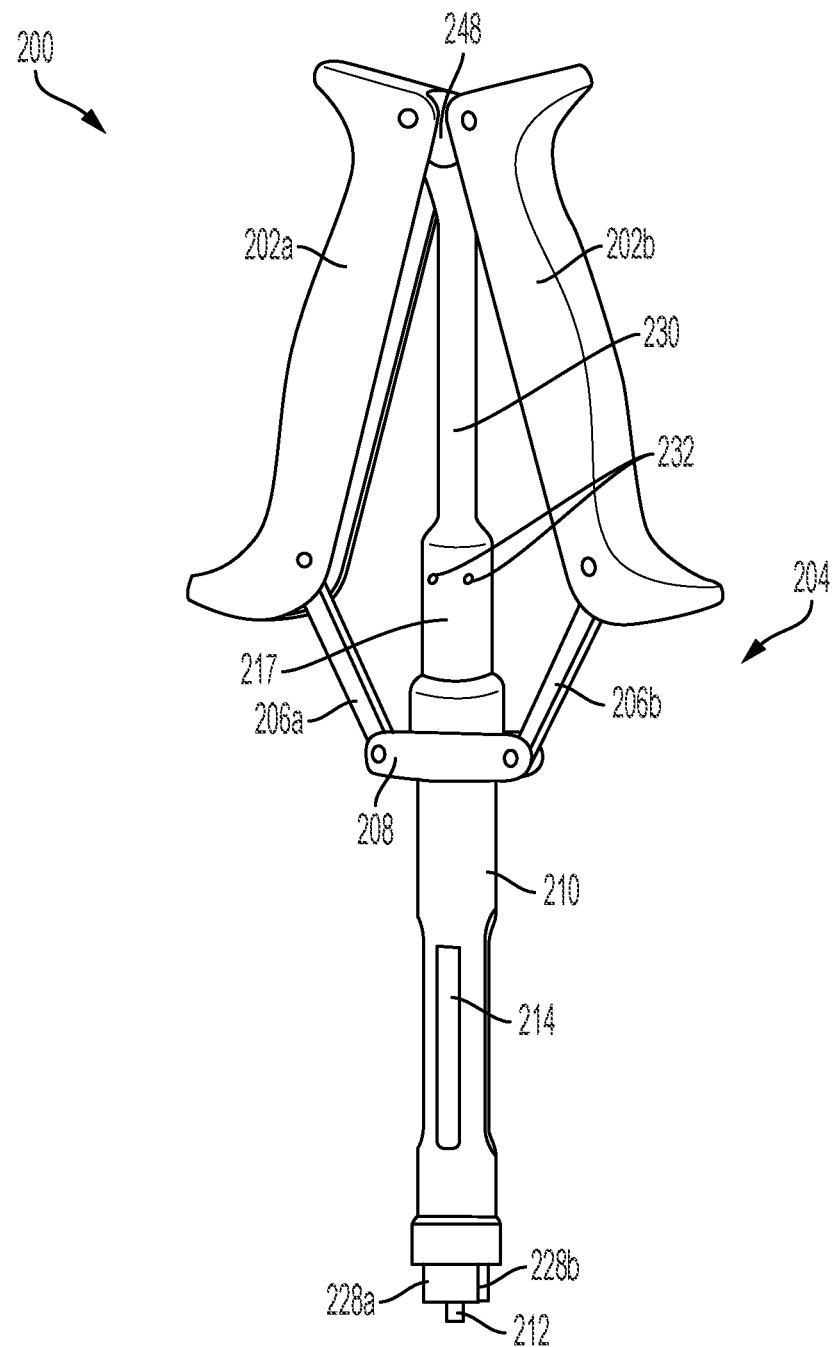
FIG. 2A is a perspective view of an example inserter, according to one or more embodiments of the present disclosure.
Figure 2B:
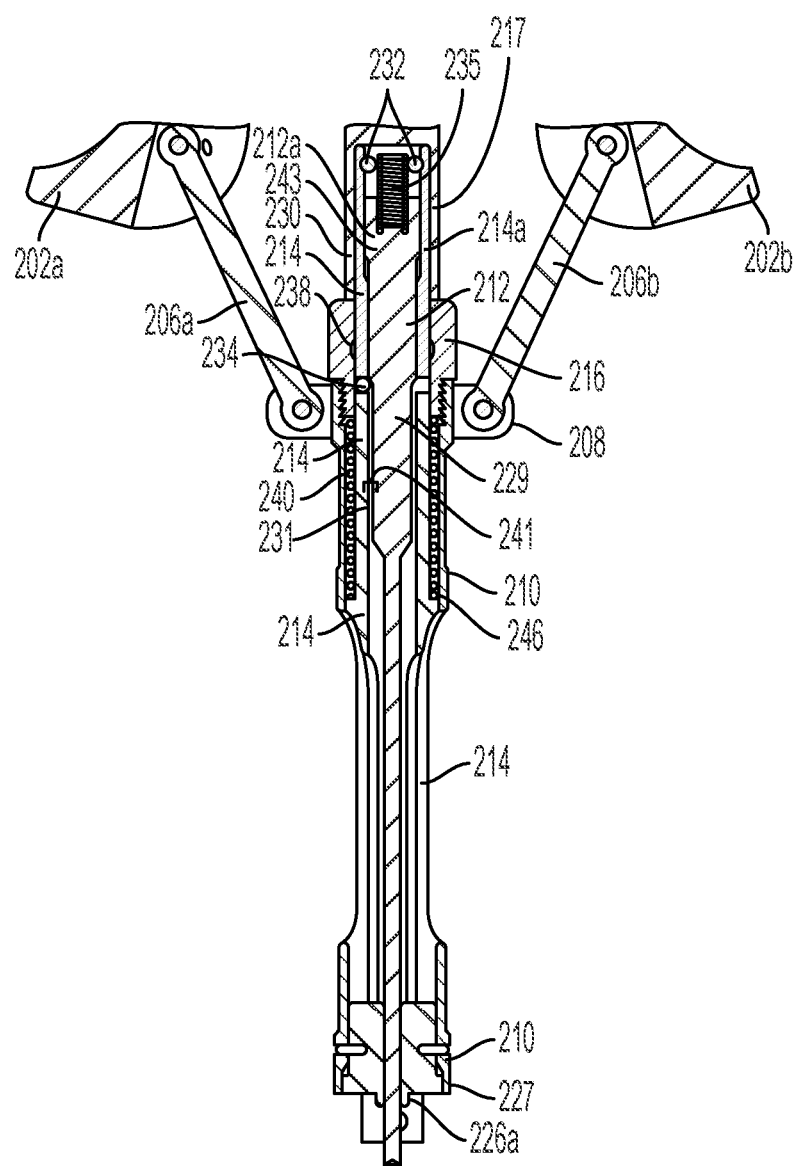
FIG. 2B-2D are cross-section views of the example inserter shown in FIG. 2A, according to one or more embodiments of the present disclosure.
Figure 2C:
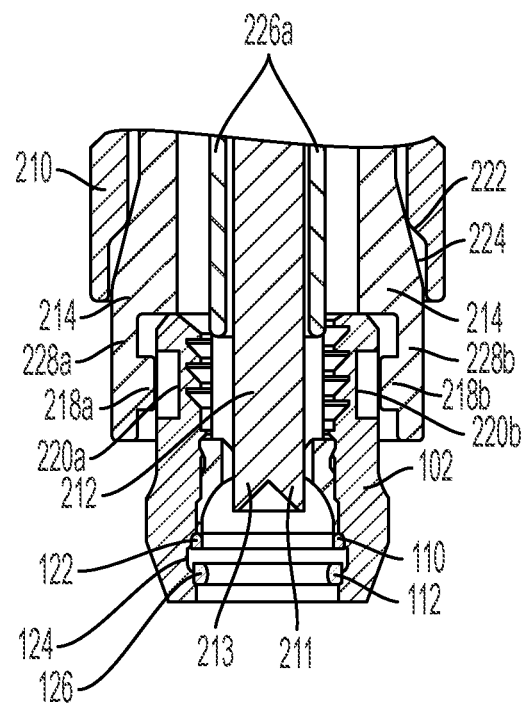
Figure 2D:
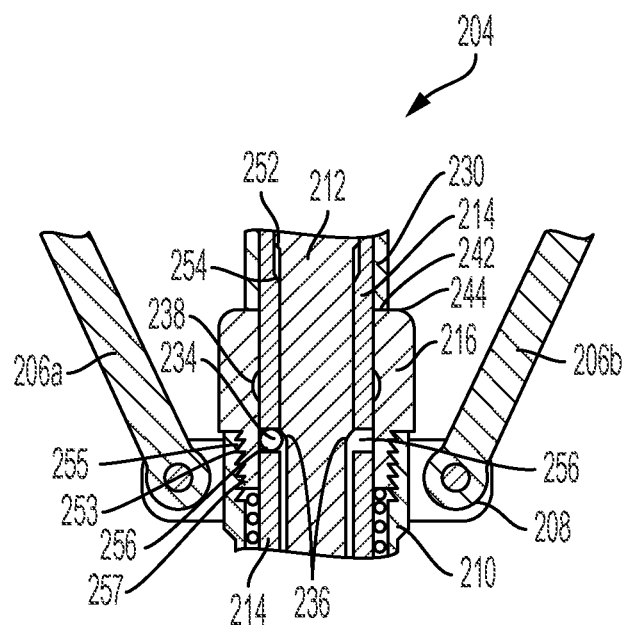
Figure 3A:
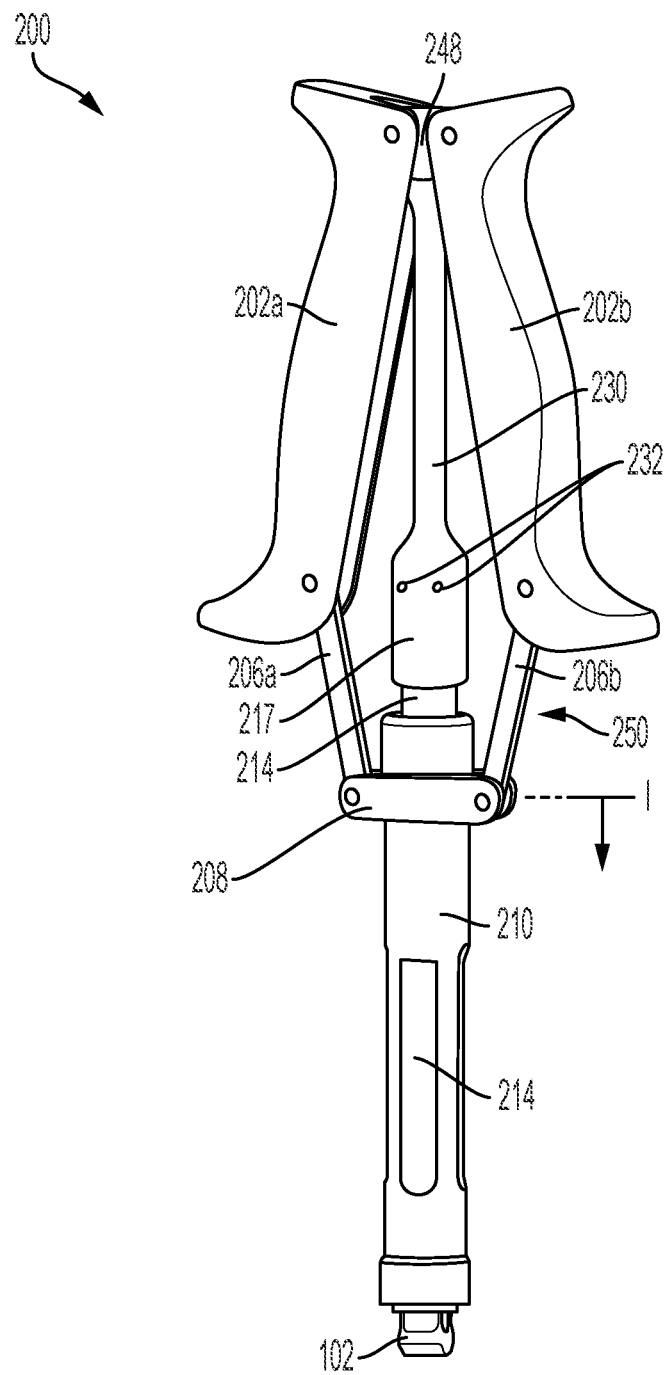
FIG. 3A is another perspective view of the example inserter shown in FIG. 2A, according to one or more embodiments of the present disclosure.
Figure 3B:
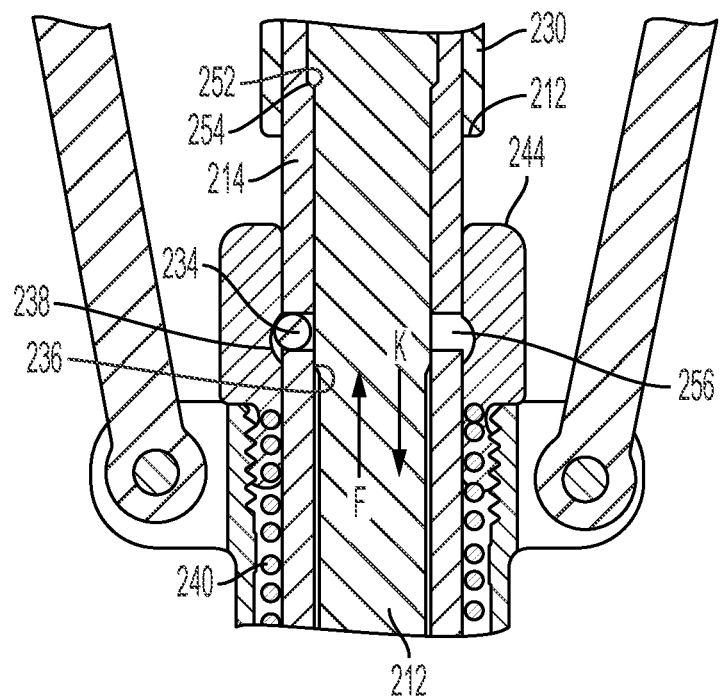
FIGS. 3B-3F are cross-section views of connecting the head assembly to the fastener of the example implant shown in FIG. 1A, via the example inserter shown in FIG. 2A, according to one or more embodiments of the present disclosure.

FIG. 2A is a perspective view of an example inserter 200, according to one or more embodiments of the present disclosure. FIG. 2B-2D are cross-section views of the example inserter 200 shown in FIG. 2A, according to one or more embodiments of the present disclosure. FIG. 3A is another perspective view of the example inserter 100 shown in FIG. 2A, according to one or more embodiments of the present disclosure.

In one or more embodiments, the inserter 200 includes at least one grasping member, such as grasping members 202a and 202b. The at least one grasping member may be a rigid structure formed in a shape to be gripped and squeezed by a user. For example, for the cases in which one grasping member is used, a user may grip a portion of the grasping member, such as grasping member 202a, and a portion of the elongated member 230, and squeeze the two components together to actuate the translation of the outer sleeve 210 and the inner sleeve 214. For the cases in which two grasping members, such as grasping members 202a and 202b, are used, the grasping members 202a and 202b may be coupled to a grasping member coupler 248 of an elongated member 230. The grasping members 202a and 202b may be rigid structures formed in a shape to be gripped and squeezed by a user. The grasping members 202a and 202b may be formed in an ergonomic shape. The two grasping members 202a and 202b may be coupled to the grasping member 248 at one end of the grasping members 202a and 202b, and coupled to an outer sleeve 210 at ends opposite the grasping member coupler 248. At the end opposite the grasping member coupler 248, the grasping member 202a is pivotably coupled to an end of a pivot link member 206a, and an opposite end of the pivot link member 206a may be pivotably coupled to the outer sleeve coupler 208. At the end opposite the grasping member coupler 248, the grasping member 202b is pivotably coupled to an end of a pivot link member 206b, and an opposite end of the pivot link member 206b may be pivotably coupled to the outer sleeve coupler 208. In one or more cases, the grasping members 202a and 202b and the pivot links 206a and 206b are configured to pivot inwards towards the elongated member 230. A user may grip the grasping members 202a and 202b and squeeze the grasping members 202a and 202b towards one another. By squeezing the grasping members 202a and 202b, the pivot links 206a and 206b move the outer sleeve 210 and the outer sleeve coupler 208 in a direction shown by the I direction in FIG. 3A.

The elongated member 230 may include an attachment end 217 disposed on an end opposite the grasping member coupler 248. The attachment end 217 may be a cylindrical receptacle configured to house an end 212a of the plunger 212 and an end 214a of the inner sleeve 214. The end 212a of the plunger 212 may be connected to a spring 235 coupled to the attachment end 217 via at least one cross pin 232. The spring 235 may be configured to bias the plunger 212 in a down position. That is, the spring 235 may apply a force on the plunger 212 to bias the plunger 212 downwards in a direction I shown in FIG. 3A.

The outer sleeve coupler 208 may be a rigid body fixedly disposed around the outer surface of the outer sleeve 210. In one or more cases, the outer sleeve coupler 208 may be integrally formed with the outer sleeve 210, such that the outer sleeve coupler 208 and outer sleeve 210 are a unibody design formed from a single structure. In one or more other cases, the outer sleeve coupler 208 may be coupled around the outer sleeve 210, in which the outer sleeve coupler 208 and the outer sleeve 210 are two separate components. The outer sleeve 210 may house a portion of an inner sleeve 214 and a portion a plunger 212, each movably disposed therein. In one or more cases, a cap 216 may be removably coupled to the end 255 of the outer sleeve 210. The end 255 of the outer sleeve 210 may include a threaded portion 253 configured to be fastened to the threaded portion 257 of the cap 216.

In one or more cases, the cap 216 may include at least one ball bearing notch 238 sized to house at least a portion of a ball bearing 234. The ball bearing notch 238 may be positioned above the outer sleeve coupler 208. The distal end 227 of the outer sleeve 210 may include a crown pusher 226a configured to move the crown 104 downwards in a direction shown by direction N in FIG. 3F. The crown pusher 226a may extend beyond the distal end 227. The crown pusher 226a may include a cylindrical cavity sized to allow the plunger 212 to move through the crown pusher 226a. In one or more cases, the crown pusher 226a may be positioned within the outer sleeve 210. The crown pusher 226a may be coupled to the outer sleeve 210. For example, the crown pusher 226a may be pinned to the outer sleeve 210. In another example, the crown pusher may be coupled to the outer sleeve 210 using another type of joining method, such as, welding or the like. In one or more cases, the crown pusher 226a and the outer sleeve 210 may be singular component forming a unitary body.

The inner sleeve 214 may be an elongated tubular member configured to extend from the attachment end 217 of the elongated member 230 to an area beyond the end 227 of the outer sleeve 210. The distal end of the inner sleeve 214 may include flexible interlocking members 228a and 228b configured to interlock with a notch, such as notches 220*a* and/or 220*b*, of the receiver 102. The notches 220*a* and 220*b* may be disposed on an outer surface of the receiver 102, in which the notches 220*a* and 220*b* face away from each other. The interlocking member 228*a* may include a protrusion 218*a* protruding from an inner surface of the interlocking member 228*a* towards the opposing interlocking member 228*a*. The protrusion 218*a* may be sized to fit within the notch 220*a* and/or 220*b*. In one or more cases, the inner sleeve 214 includes at least one ball bearing receiver 256 sized to receive at least a portion of the ball bearing 234. The at least one ball bearing receiver 256 may be disposed within the wall of the inner sleeve 214.

In one or more cases, the plunger 212 is an elongated rod having the end 212*a* connected to the attachment end 217 of the elongated member 230, and an opposing end 213 including the mating surface 211. A middle portion 229 of the plunger 212 and an inner surface 231 of the inner sleeve 214 may be separated by a gap 241.

The plunger 212 may include one or more tapered surfaces, such as a lower tapered surface 236 and an upper tapered surface 252, for engaging the plunger 212 in different positions with the inner sleeve 214. For example, for the cases in which the plunger 212 is retracted in an up position, the ball bearing 234 may be positioned within the ball bearing receiver 256 and a portion of the ball bearing 234 may extend into the gap 241. The portion of the ball bearing 234 may contact the lower tapered surface 236 of the plunger 212 and may prevent the plunger 212 from moving in a direction towards the end 227 of the outer sleeve 210. In another example, for the cases in which the plunger 212 is configured in a down position, the spring 235 may bias the plunger 212 downwards such that the ball bearing 234 may be positioned within the ball bearing receiver 256 and a portion of the ball bearing 234 may extend into the ball bearing notch 238. The upper tapered surface 252 may be disposed on an upper portion 243 of the plunger 212. The ball bearing 234 may be removed from the inner diameter of the inner sleeve 214, thereby allowing the tapered surface 236 of the plunger 212 to extend beyond the ball bearing receiver 256. When extending beyond the ball bearing receiver 256, the plunger 212 may move towards the end 277 of the outer sleeve 210 until the upper tapered surface 252 contacts the interfacing surface 254 positioned on the inner surface of the inner sleeve 214. The interfacing surface 254 may have a shape corresponding to the upper tapered surface 252. The interfacing surface 254 may prevent the upper portion 243 of the plunger 212 from moving beyond the interfacing surface 254, and therefore limiting the overall distance that the plunger 212 can move within the inner sleeve 214.

In one or more cases, the inserter 200 may include a spring 240 housed between the inner surface of the outer sleeve 210 and the outer surface of the inner sleeve 214. The cap 216 may be used to retain the spring 240 within the area defined by the inner surface of the outer sleeve 210 and the outer surface of the inner sleeve 214. The spring 240 may provide tension force to move the tensioner between the open position 204, as shown in FIG. 2A, and the locked position 250, as shown in FIG. 3A. In one or more cases, as the grasping members 202*a* and 202*b* are compressed into the locked position 250, and thereby translating the outer sleeve 210 over the inner sleeve 214, the spring 240 may decompress providing a force to facilitate the grasping members 202*a* and 202*b* returning to the open position 204. For the cases in which the spring 240 is to be replaced, the cap 216 may be removed to allow the spring 240 to be removed and a new spring to be inserted in its place, after which the cap 216 may be reinstalled on the end 255 of the outer sleeve 210.

In one or more cases, in the open position 204, the bottom surface 242 of the elongated member 230 may be in contact with the upper surface 244 of the outer sleeve 210. In one or more cases, in the open position 204, the flexible interlocking members 228*a* and 228*b* may be in a relaxed state, as shown in FIGS. 2B-2D, and not compressed towards one another. In the open position 204, the plunger 212 is retracted in the up position, as shown in FIG. 2B-2D. In the up position, the ball bearing 234 may be positioned within the ball bearing receiver 256 and a portion of the ball bearing 234 may extend into the gap 241. The portion of the ball bearing 234 may contact the lower tapered surface 236 of the plunger 212 and may prevent the plunger 212 from moving towards the end 227 of the outer sleeve 210.

FIGS. 3B-3F are cross-section views of connecting the head assembly 101 to the fastener 106 of the example implant 100 shown in FIG. 1A, via the example inserter 100 shown in FIG. 2A, according to one or more embodiments of the present disclosure.

Figure 3C:
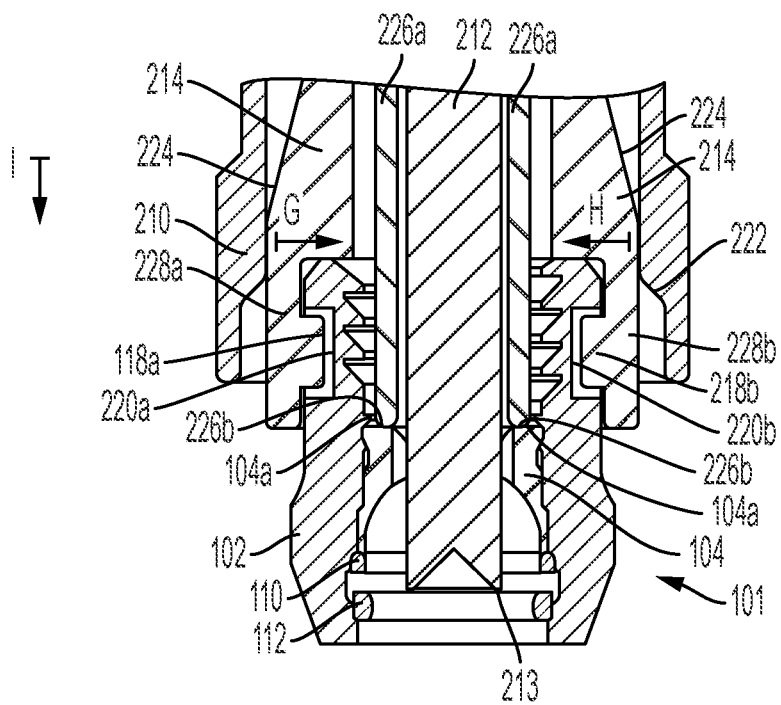

In one or more cases, while in the up position, the head assembly 101 may be inserted between interlocking members 228*a* and 228*b* of the inner sleeve 214, as shown in FIG. 2B-2D, to begin coupling the head assembly 101 to the inserter 100. A user may squeeze the grasping members 202*a* and 202*b* inwards to translate the outer sleeve 210 over the inner sleeve 214, as shown in FIG. 3A. As the inner sleeve 214 is retracted within the outer sleeve 210, in a direction F shown in FIG. 3B, the ball bearing receiver 256 and ball bearing 234 may align with the ball bearing notch 238, in which the spring 235 forces the lower tapered surface 236 of the plunger 212 to move downwards in a direction K shown in FIG. 3B, thereby moving a portion of the ball bearing 234 into the ball bearing notch 238 and allowing the lower tapered surface 236 of the plunger 212 to move in the direction K beyond the ball bearing receiver 256. Moreover, as the inner sleeve 214 is retracted within the outer sleeve 210, in a direction F shown in FIG. 3B, the outer surface 224 of the interlocking members 228*a* and 228*b* may contact the inner protruded surface 222 of the outer sleeve 210, thereby causing the flexible interlocking members 228*a* and 228*b* to flex inwards in directions G and H respectively, as shown in FIG. 3C.

As the user squeezes the grasping members 228*a* and 228*b* further into the locked position 250, the plunger 212 may extend beyond the end 227 of the outer sleeve 210. The plunger 212 may extend beyond the end 227 of the outer sleeve 210 until the upper tapered surface 252 contacts the interfacing surface 254 positioned on the inner surface of the inner sleeve 214. In the locked position 250, the distal end 226*b* of the crown pusher 226*a* is positioned near the proximal surface 104*a* of the crown 104, and the end 213 of the plunger 212 is positioned within the receiving portion 114*a*, as shown in FIG. 3C.

In one or more cases, to lock the head assembly 101 on the head 108 of the fastener 106 that is fixed in a body, for example, a vertebra, the mating surface 211 of the plunger 212 is aligned with the mating surface 116 of the fastener 106, and the inserter 100 and the receiver 102 are placed onto the head 108 of the fastener 106. In one or more other cases, the head assembly 101 may be locked on the head 108 by mating the mating surface 211 with the lead-in chamfer and/or counter sink of the head 108. As the receiver 102 translates onto the head 108, the surface 105 of the head 108 may contact the lower retainer 112 and move the lower retainer 112 into the expansion chamber 124, as shown by the B direction in FIG. 1D. In the expansion chamber 124, the lower retainer 112 expands to a size, in which the head 108 may pass though the inner diameter of the lower retainer 112, as the head 108 passes through the inner diameter of the lower retainer 112. The head 108 is pressed against the inner surface 118 of the crown 104 in a direction C as shown in FIG. 1E, and the lower retainer 112 moves to a distal end of the head 108, in a direction D as shown in FIGS. 1F and 3F.

Figure 3D:
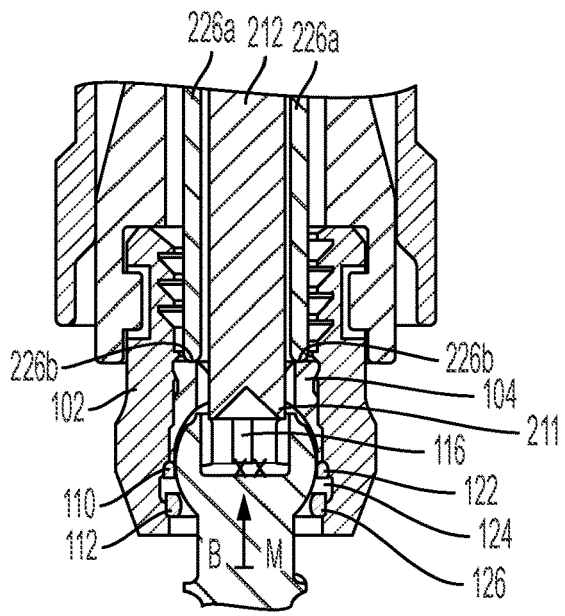
Figure 3E:
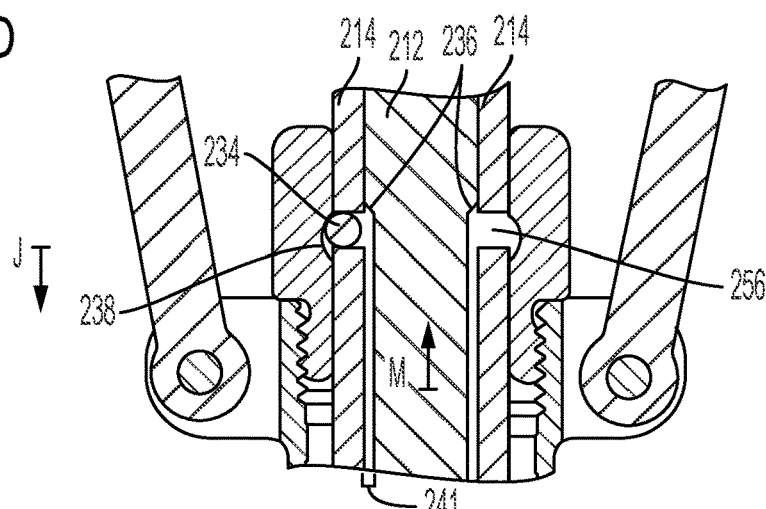
Figure 3F:
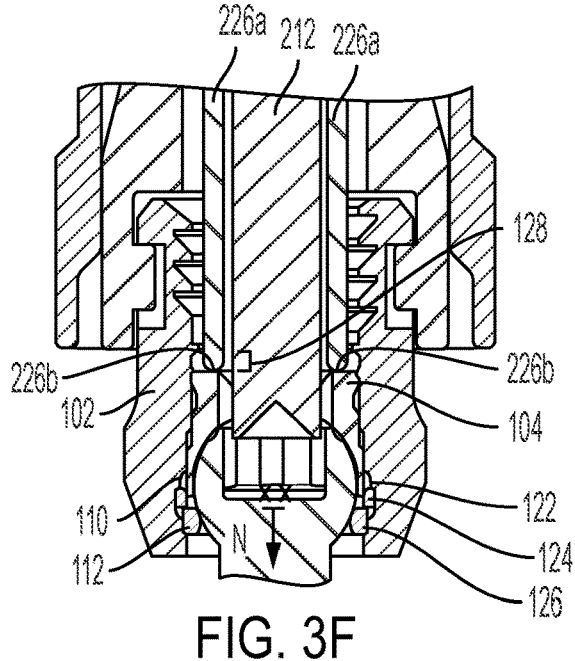

Moreover, as the receiver 102 translates onto the head 108, the mating surface 116 contacts the mating surface 211 of the plunger 212 and causes the plunger 212 to move in an upward direction shown by direction M in FIGS. 3D and 3E. The plunger 212 moves upward such that the spring 235 is compressed and the lower tapered surface 236 of the plunger 212 moves above the ball bearing receiver 256, as shown in FIG. 3E. The ball bearing 234 moves inwards from the ball bearing notch 238 towards the lower tapered surface 236. The user may further squeeze the grasping members 202a and 202b causing the crown pusher 226a to force the crown 104 into the receiving portion 114a, in a direction show by arrow N in FIG. 3F and direction E in FIG. 1G. The crown pusher 226a may move the crown 104 downwards in the receiving portion 114a, in which the ends 129 of the crown 104 move the upper retainer 110 out of the upper chamber 122 and into the expansion chamber 124. In the expansion chamber 124, the upper retainer 110 expands such that the upper surface 127 of the upper retainer 110 interfaces with the upper rim 123 of the expansion chamber 124. In this state, the lower retainer 112 may no longer enter into the expansion chamber 124, thereby locking the head assembly 101 onto the head 108 of the fastener 106, as shown in FIGS. 1G, 1H, and 3F.

To remove the inserter 100 from the implant 100, the user releases the user's grip on the grasping members 202a and 202b. The compressed spring 240 may decompress providing a force that facilitates the grasping members 202a and 202b to return to the open position 204. By returning to the open position 204, the interlocking members 228a and 228b and the notches 220a and 220b of the receiver 102 are uncoupled from one another and the inserter 100 may be removed from the implant 100.

Figure 4A:
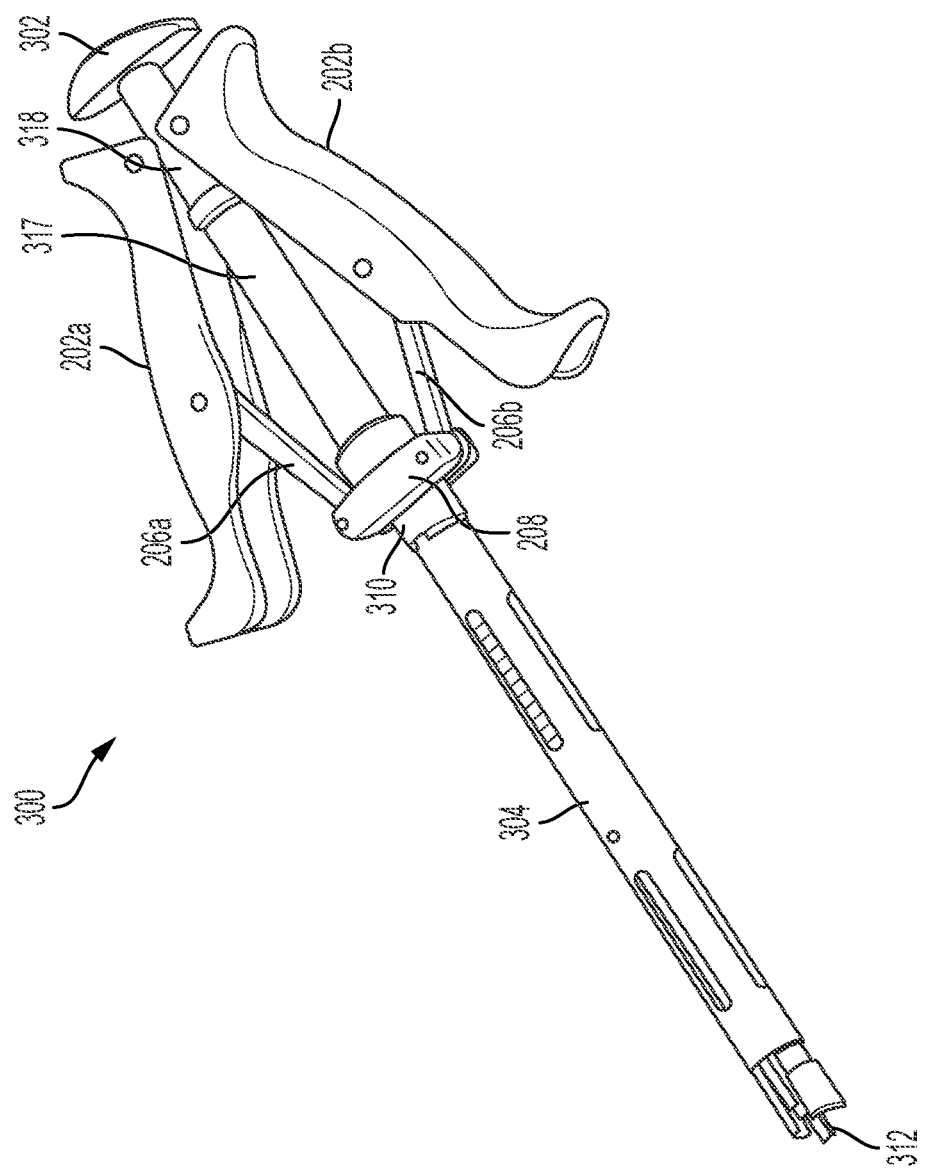
FIG. 4A is a perspective view of another example inserter, according to one or more embodiments of the present disclosure.
Figure 4B:
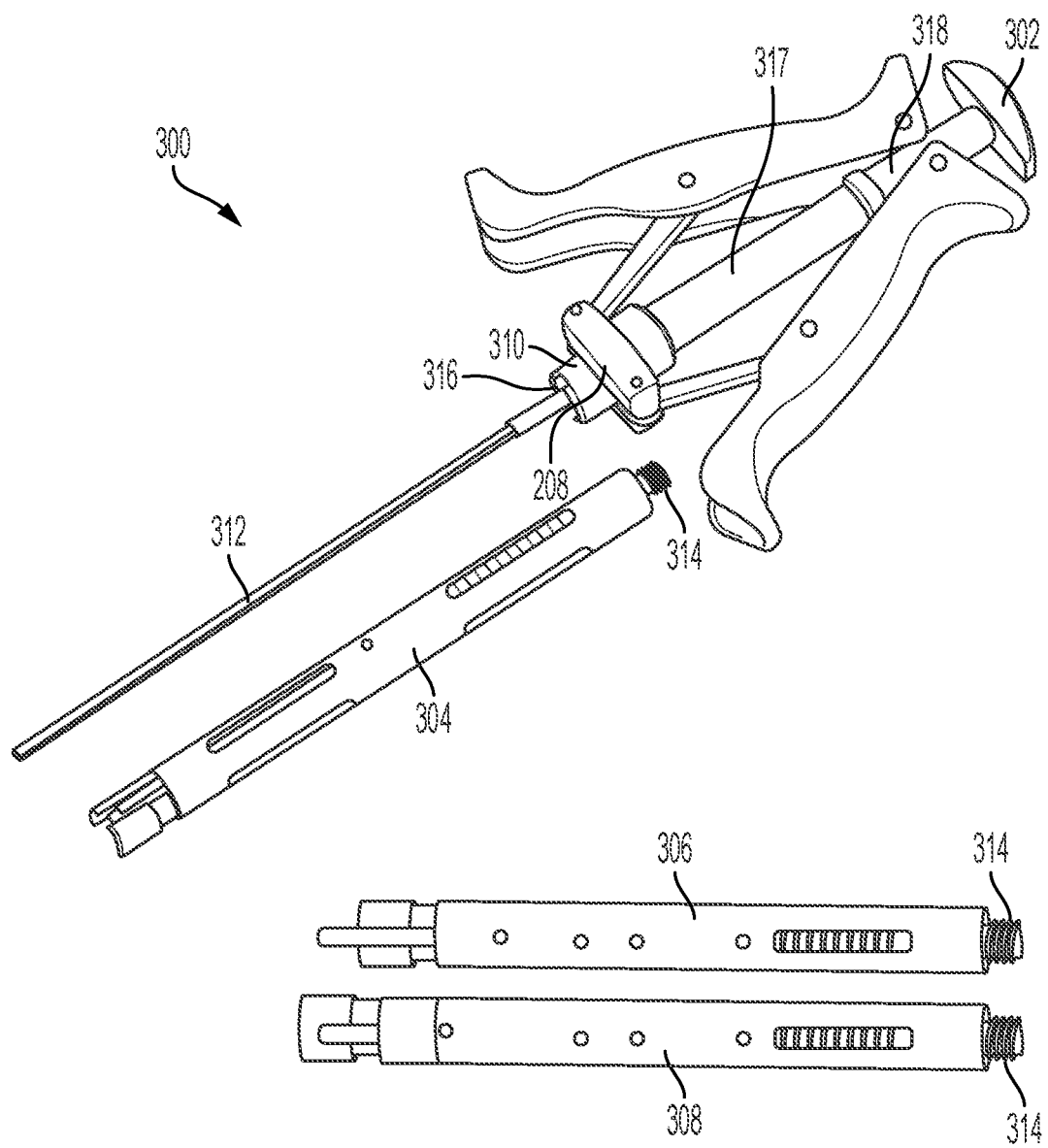
FIG. 4B is a break away perspective view of the example inserter as shown in FIG. 4A, according to one or more embodiments of the present disclosure.
Figure 4C:
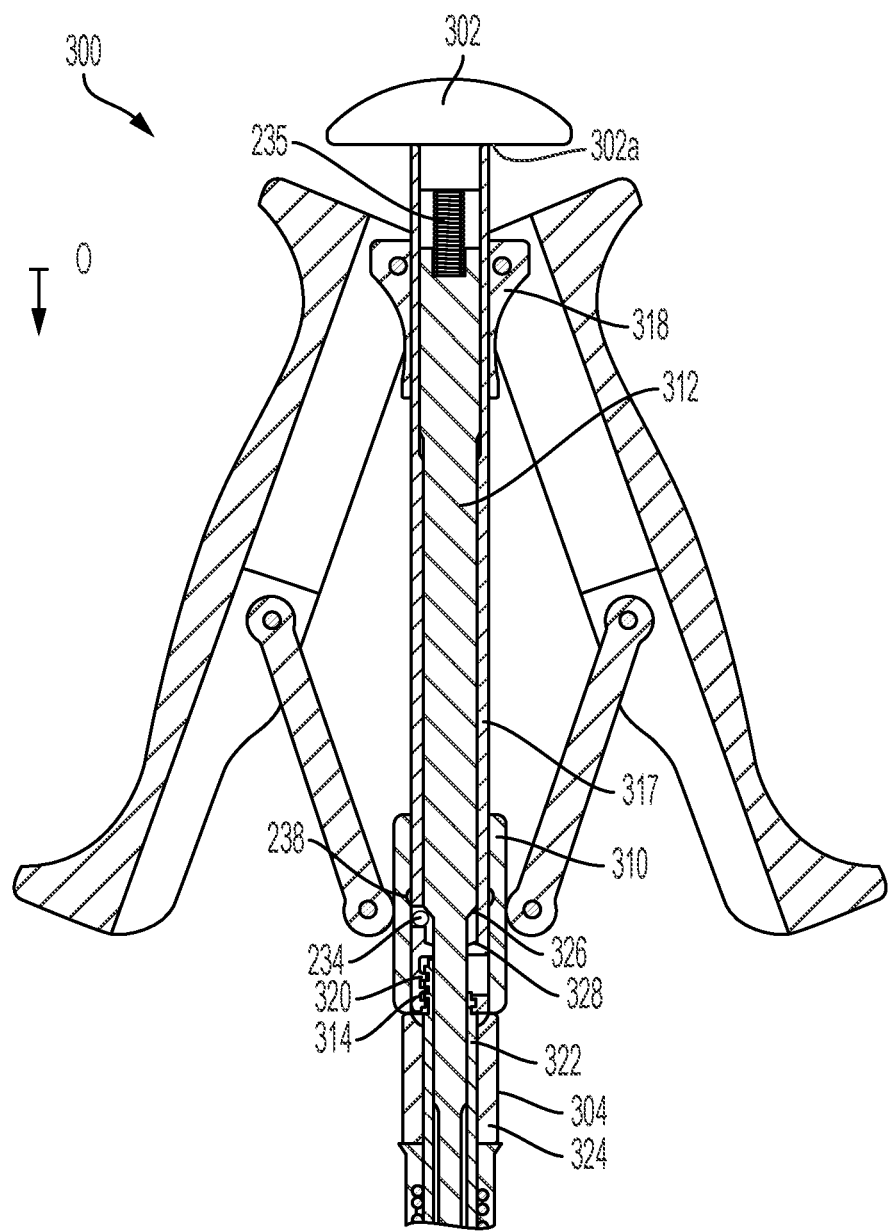
FIG. 4C is a cross-section view of the example inserter as shown in FIG. 4A, according to one or more embodiments of the present disclosure.

FIG. 4A is a perspective view of another example inserter 300, according to one or more embodiments of the present disclosure. FIG. 4B is a break away perspective view of the example inserter 300 as shown in FIG. 4A, according to one or more embodiments of the present disclosure. FIG. 4C is a cross-section view of the example inserter 300 as shown in FIG. 4A, according to one or more embodiments of the present disclosure.

In one or more embodiments, the inserter 300 may be modular such that a working end, such as working end 304, may be swapped out for another working end, such as working end 306, in order to accommodate head assemblies having different configurations. For example, working end 304 may be installed on the inserter 300, in which the working end 304 is configured to be used with the head assembly 101. In other examples, working end 306 and working end 308 may be installed on the inserter 300. Working ends 304, 306, and 308 may each be configured to interface with a different style of the head assembly 101, e.g., a head assembly of a uniaxial screw, a head assembly of a multiaxial screw (MAS), a head assembly of a reduction head multiaxial screw (RMAS), or a head assembly of an extended tab MAS. Working ends 304, 306, and 308 may each be formed in a variety of lengths such that the distance in which the insertion end of the plunger 312 into the head assembly 101 and/or the mating surface 115 of the fastener 106 remains uniform for each working end attached to the inserter 300. For example the lengths of the working ends 304, 306, and 308 may range from about 4.5 inches to about 6.25 inches. In an example, working end 304 may be 4.75 inches in length, working end 306 may be 5.5 inches in length, and working end 308 may be 6.0 inches in length.

In one or more cases, the inserter 300 includes grasping members 202a and 202b pivotably coupled to a grasping member coupler 318 at one end. The grasping members 202a and 202b may each be pivotably coupled to an end of pivot link 206a and pivot link 206b, respectively, in a middle portion of each grasping member. An opposite end of each pivot link 206a and 206b may be pivotably coupled to the outer sleeve coupler 208. In one or more cases, the outer sleeve coupler 208 may be formed around the working end attachment 310. In one or more cases, the outer sleeve coupler 208 may be integrally formed with the working end attachment 310, such that the outer sleeve coupler 208 and working end attachment 310 are a unibody design formed from a single structure. In one or more other cases, the outer sleeve coupler 208 may be coupled around the working end attachment 310, in which the outer sleeve coupler 208 and the working end attachment 310 are two separate components. The working end attachment 310 may include a thread portion 320 on a receiving end 316 of the working end attachment 310.

An elongated member 317 may be a tubular body sized to allow a plunger 312 to translate therethrough. The working end attachment 310 may be coupled to an end of an elongated member 317, and the grasping member coupler 318 may be attached to an opposite end of the elongated member 317. The elongated member 317 may be a rigid tubular body configured to allow the grasping members 202a and 202b be compressed towards one another. An impact cap 302 may be attached to the distal end of the elongated member 316. The impact cap 302 may be rigidly interfaced with the elongated member 317. In one or more cases, the impact cap 302 may be used to push the inserter 300 downwards. For example, when attached the head assembly 101 to the fastener 106, a user may place his or her hand on the impact cap 302 and push downwards to facilitate the translation of the head assembly 101 over the fastener 106. The inner surface 302a of the impact cap 302 may prevent the plunger 312 from translating farther through the elongated member 317 and the outer sleeve 324, in a direction O shown in FIG. 4C, beyond a selected distance. The elongated member 317 includes the spring 235 coupled to the impact cap 302 and an end of the plunger 312. The spring 235 may be configured to bias the plunger 312 in a down position. The spring 235 may aid in facilitating the translation of the plunger 312 through the elongated member 317 and the outer sleeve 324.

In one or more cases, the working end 304 includes the outer sleeve 324 and the inner sleeve 322. The proximal end of the inner sleeve 322 include a threaded portion 314 configured to fasten to the threaded portion 320 of the working end attachment 310. To attach the working end 304 to the working end attachment 310, the plunger 312 is inserted through the inner sleeve 322 and the threaded portion 320 and the threaded portion 314 are threaded together, thereby fastening the working end 304 to the working end attachment 310. In one or more other cases, the working end 304 and the working end attachment 310 may be fastened to one another via another connection means such as quick release mechanism, push button mechanism, or any other releasably coupled interface. In some embodiments the threaded portion 320 and threaded portion 314 are timed threads such that the grasping members 202a and 202b and the working end 304 are positioned in a consistent manner.

Having connected the working end 304 to the working end attachment 310, the elongated member 316 and the inner sleeve 322 are coupled to one another and are configured to move in unison in a similar manner as the inner sleeve 214.

The outer sleeve 324 includes one or more of the same or similar features as outer sleeve 310. The plunger 312 includes one or more of the same or similar features as plunger 212. The tapered surface 326 includes one or more of the same or similar features as the lower tapered surface 236. The inserter 300 and working end 304 are configured to lock the head assembly 101 to the fastener 106 in a same or similar fashion as inserter 100. Accordingly, a description of such features is not repeated. Working ends 306 and 308 may attach to the inserter 300 in a same or similar fashion as working end 304. Accordingly, a description of working ends 306 and 308 is not repeated.

Figure 5A:
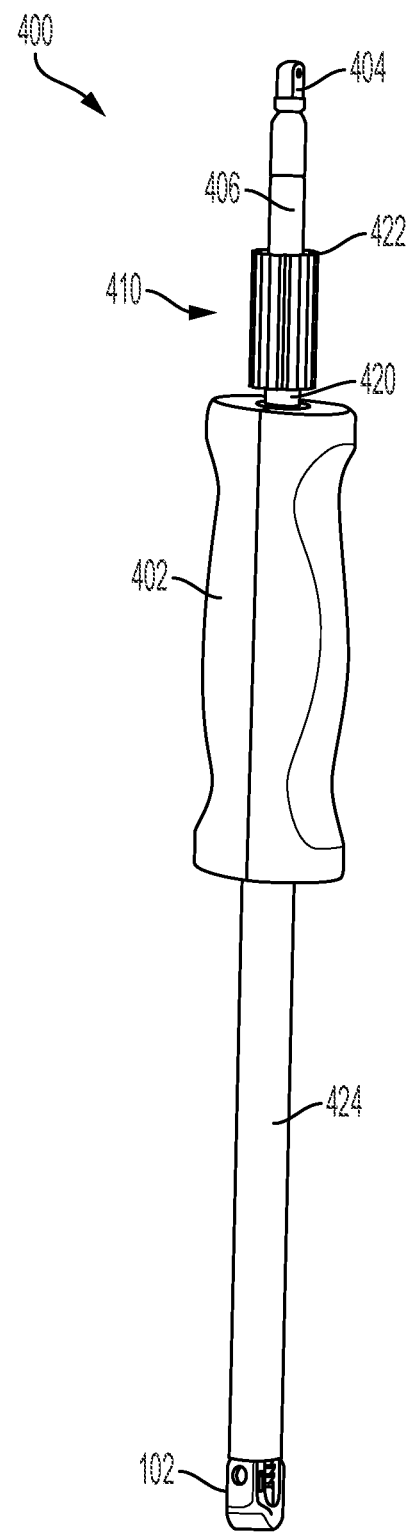
FIG. 5A is a perspective view of another example inserter, according to one or more embodiments of the present disclosure.
Figure 5B:
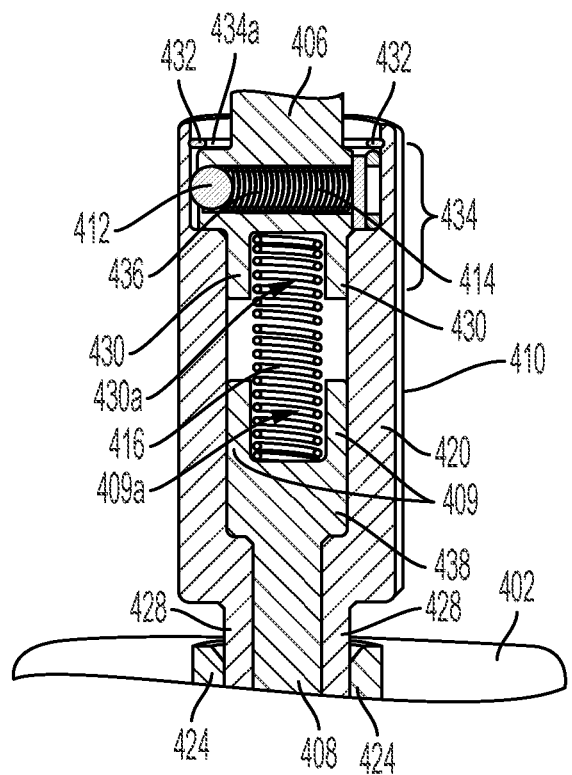
FIGS. 5B-5C are cross-section views of the example inserter shown in FIG. 5A, according to one or more embodiments of the present disclosure.
Figure 5C:
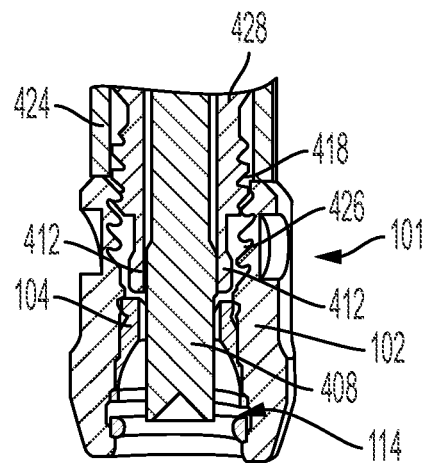
Figure 5D:
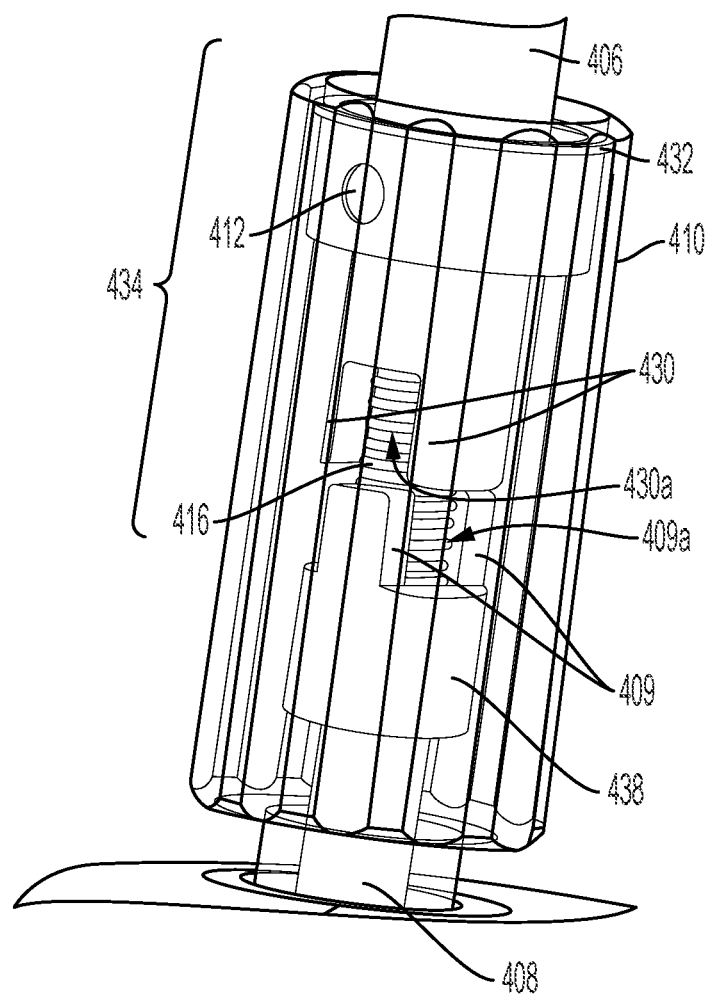
FIG. 5D is a transparent perspective view of the example inserter as shown in FIG. 5A, according to one or more embodiments of the present disclosure.

FIG. 5A is a perspective view of another example inserter 400, according to one or more embodiments of the present disclosure. FIGS. 5B-5C are cross-section views of the example inserter 400 shown in FIG. 5A, according to one or more embodiments of the present disclosure. FIG. 5D is a transparent view of the example inserter 400 as shown in FIG. 5A, according to one or more embodiments of the present disclosure.

In one or more embodiments, the inserter 400 includes a handle 402 coupled to an outer sleeve 424 and a spring loaded clutch 410. A portion of the outer sleeve 424 may be disposed within and coupled to the handle 402. The outer sleeve 424 may be an elongated tubular member configured to allow an inner sleeve 428 and a plunger 408 to translate therein.

An elongated member 406 may be attached to an upper end 422 of the spring loaded clutch 410. The elongated member 406 may be a rigid rod, in which one end includes a mating surface 404 and an opposing end 434 that is rotatably coupled within the spring loaded clutch 410. The mating surface 404 may be configured to receive a handle to facilitate the rotation of the elongated member 406. The elongated member 406 may be rotated in a clockwise or a counterclockwise manner.

The opposing end 434 of the elongated member 406 may include a horizontal cavity 436 that houses a top horizontal spring 414 and a spring loaded ball 412. A ring 432 may be positioned on an outer surface 434a of the opposing end 434 and within a portion of the spring loaded clutch 410. The ring 432 may be formed in a "C" shape. The opposing end 434 of the elongated member 406 may include protrusions 430 that extend from beneath the horizontal cavity 436 towards the handle 402. The protrusions 430 may be configured to encompass an end portion of a vertical spring 416. The protrusions 430 may include recesses 430a between each side of the protrusion 430. For example, the protrusions 430 and one of the recesses 430a may form a "U" joint type of interface. In an example, the opposing end 434 may include two protrusions as shown in FIGS. 5A-5D. However, it is noted that the opposing end 434 may include more than two protrusions or only one protrusion. A proximal end 438 of the plunger 408 may be cylindrically formed to engage an end of the vertical spring 416 therein. The proximal end 438 may include protrusions 409 that extend from the proximal end 438 away from the handle 402. The protrusions 409 may be configured to encompass an end portion of the vertical spring 416. The protrusions 409 may include a recess 409a between each side of the protrusion 409. For example, the protrusions 409 and one of the recesses 409a may form a "U" joint type of interface. The protrusions 409 and 430 may be configured to interlock with one another. For example, the protrusions 409 may be configured to fit within recesses 430a, and the protrusions 430 may be configured to fit within recesses 409a. The vertical spring 416 may be positioned between protrusions 430 and 409 in a pretensioned state (i.e., a compressed state). The vertical spring 416 may bias the plunger 408 in a down position. The ring 432 may be configured to hold the opposing end 434 within the spring loaded clutch 410 and maintain the vertical spring 416 in the pretensioned state.

In one or more cases, if the clutch 410 is not positioned for head attachment, the elongated member 406 may spin freely. The clutch 410 may not be configured for head attachment when the protrusions 409 are not aligned with the recesses 430 and/or the protrusions 430 are not aligned with the recesses 409a, as shown in FIG. 5A.

In one or more cases, the spring loaded ball 412 and top horizontal spring 414 may click when the clutch 410 is positioned for head attachment. The clutch 410 may be positioned for head attachment by rotating the elongated member 406. The clutch 410 may be positioned when the recess 430a is aligned over protrusion 409 and the recess 409a is aligned under the protrusion 430, such that the protrusions 409a and 430 may interlock with one another, as shown in FIG. 5D. That is, the plunger 412 may be keyed to the elongated member 406. For the cases in which the clutch 410 is positioned for head attachment, the elongated member 406 may be pressed down and/or the fastener 106 may be engaged with the head assembly 101, in which the protrusions 409a may engage with the recesses 430a and the protrusions 430 may engage with the recesses 409a. That is, the elongated member 406 may move downwards to engage with the plunger 412, and/or the plunger 412 may move upwards to engage with the elongated member 406.

For the one or more cases, in which the plunger 412 and the elongated member 406 are interlocked via protrusions 409 and 430, the receiver interface 418 of the inner sleeve 428 may be coupled to the receiver interface 426 of the receiver 102. The receiver interface 418 and the receiver interface 426 may each be threaded and configured to mate with one another. As the receiver interface 418 is threaded into the receiver interface 426, the crown pusher 412 may engage the crown 104 and push the crown 104 into the receiver base 114. To remove the inserter 400 from the head assembly 101, the receiver interface 418 is unthreaded from the receiver interface 426.

Figure 6A:
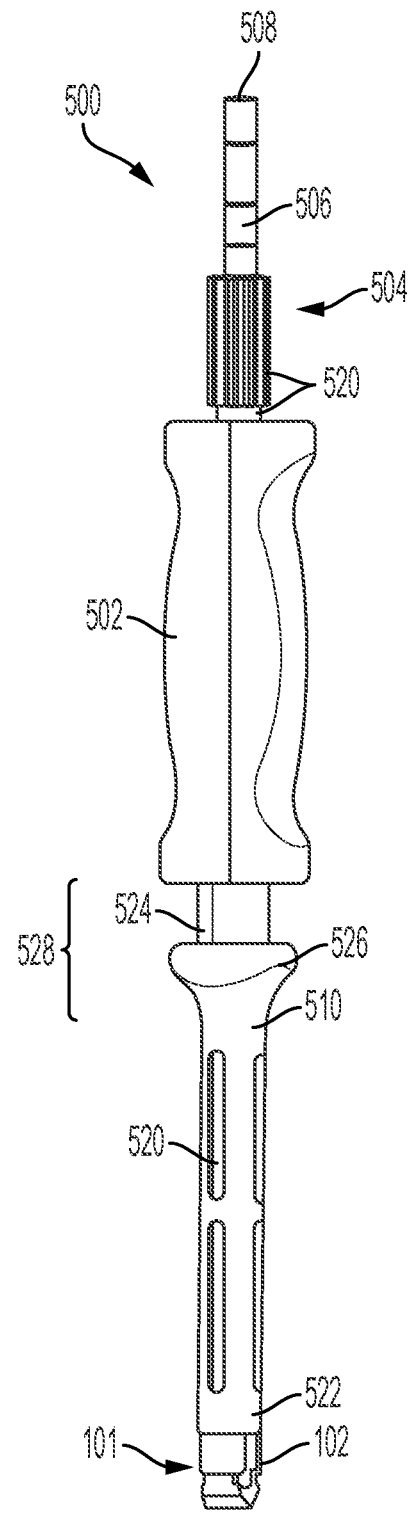
FIG. 6A is a perspective view of another example inserter, according to one or more embodiments of the present disclosure.
Figure 6B:
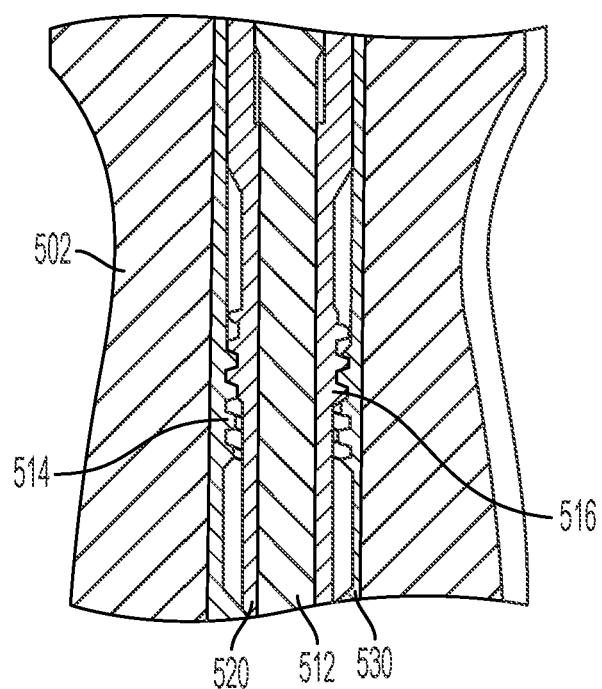
FIG. 6B is a cross-section view of the example inserter shown in FIG. 6A, according to one or more embodiments of the present disclosure.

FIG. 6A is a perspective view of another example inserter 500, according to one or more embodiments of the present disclosure. FIG. 6B is a cross-section view of the example inserter 500 shown in FIG. 6A, according to one or more embodiments of the present disclosure.

In one or more embodiments, the inserter 500 includes a handle 502 coupled to an inner sleeve 520 and a spring loaded clutch 504. A portion of the inner sleeve 520 may be disposed within and coupled to the handle 502. The spring loaded clutch 504, elongated member 506, inner sleeve 520, and mating surface 508 may include one or more of the same or similar features of the spring loaded clutch 420, elongated member 406, inner sleeve 408, and mating surface 404. Accordingly, a description of such features is not repeated.

A spring loaded sleeve 510 may be an elongated tubular member having a spring loaded end 528 and an interlocking end 522 opposite the spring loaded end 528. The spring load sleeve 510 may be configured to translate over the inner sleeve 520. The interlocking end 522 may include interlocking members similar to interlocking members 228a and 228b. The interlocking members on the interlocking end 522 may be configured to interlock with the notches 220a and 220b of the receiver 102. The spring loaded end 528 may include a spring portion 524 housed within the spring loaded end 528 and a handle 526 configured to translate over the spring portion 524. The handle 526 may be formed in an ergonomic shape to facilitate a user moving the spring loaded sleeve 228 over the inner sleeve 520

In one or more cases, the handle 502 includes an outer sleeve 530 rigidly attached to one another and configured to house a portion of the plunger 512 and the inner sleeve 520. The outer sleeve 530 may include a threaded portion 514 configured to engage a threaded portion 516 of the inner sleeve 520. When the clutch 504 is engaged, i.e., when the protrusions within the clutch 504 are interlocked with one another, the inner sleeve 520 may be rotated within the outer sleeve 530 to thread the threaded portion 516 into the threaded portion 514.

To load the head assembly 101 within the interlocking end 522, the spring loaded sleeve 228 is retracted towards the handle 502 in a locked position, thereby exposing the inner sleeve 520 and the plunger 512. The spring loaded sleeve 510 is unlocked and may translate over the inner sleeve 520 and the interlocking end 522 may interlock with the receiver 102. The clutch 504 may be engaged such that the inner sleeve 520 may be rotated within the outer sleeve 530 to thread the threaded portion 516 into the threaded portion 514. As the inner sleeve 520 is threaded through the outer sleeve 530, the crown pusher may engage the crown 104 and push the crown 104 into the receiver base 114. To remove the inserter 500 from the head assembly 101, the inner sleeve 520 is unthreaded from the outer sleeve 530, and the spring loaded sleeve 228 is retracted towards the handle 502 in a locked position, thereby uncoupling the head assembly 101 from the inserter 500.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:
an elongated first member;
a first tubular member, a portion of the elongated first member being positioned within the first tubular member;
a second tubular member, the portion of the elongated first member and a portion of the first tubular member being positioned within the second tubular member; and
at least one grasping member,
wherein a portion of the at least one grasping member is pivotably coupled to the first tubular member and another portion of the at least one grasping member is pivotably coupled to the second tubular member,
wherein the at least one grasping member is configured to actuate translation of the first tubular member and the second tubular member,
wherein the elongated first member is configured to translate within a portion of the first tubular member based on a position of the first tubular member with respect to the second tubular member, and
wherein in an open position, the elongated first member and the portion of the first tubular member are configured to translate through the second tubular member in unison.

2. The surgical instrument of claim 1, wherein the first tubular member comprises an inner tubular member and an elongated second member, and
wherein an end of the elongated second member is coupled to at least one of the elongated first member and the inner tubular member.

3. The surgical instrument of claim 1, wherein an end of the first tubular member comprises interlocking portions each configured to interlock with a portion of a head assembly.

4. The surgical instrument of claim 3, wherein as the second tubular member translates over a portion of the first tubular member, an end of the second tubular member is configured to compress the end of the tubular inner member.

5. The surgical instrument of claim 1, wherein in a locked position, the elongated first member is configured to translate through the second tubular member independent of the first tubular member.

6. The surgical instrument of claim 1, further comprising a ball bearing,
wherein the portion of the first tubular member comprises a ball bearing receiver sized to house a portion of the ball bearing.

7. The surgical instrument of claim 6, wherein the elongated first member comprises an angular surface configured to engage a surface of the ball bearing.

8. The surgical instrument of claim 7, wherein when the angular surface is engaged with the surface of the ball bearing, the ball bearing prevents an end of the elongated first member from translating in a direction towards a compression end of the second tubular member.

9. The surgical instrument of claim 6, wherein the second tubular member comprises a ball bearing notch disposed within an end of the second tubular member opposite the compression end and sized to house a portion of the ball bearing.

10. The surgical instrument of claim 9, wherein when a portion of the ball bearing is housed within the ball bearing notch, the elongated first member is configured to translate through the second tubular member independent of the first tubular member.

11. A modular surgical instrument comprising:
an elongated first member;
an elongated second member having a first end and a second end disposed on an opposite side of the first end, the first end comprising a working end attachment;
at least one grasping member; and a first working end comprising:
a first interlocking portion disposed on a proximal end of the first working end and configured to interlock with a second interlocking portion disposed on a proximal end of the working end attachment,
a first tubular member, a portion of the elongated first member being positioned within the first tubular member,
a second tubular member, the portion of the elongated first member and a portion of the first tubular member being positioned within the second tubular member,
wherein a portion of the at least one grasping member is pivotably coupled to the first tubular member and another portion of the at least one grasping member is pivotably coupled to the first end of the elongated second member, wherein the first working end is removably coupled to the first end of the elongated second member, via the first interlocking portion and the second interlocking portion, and wherein the at least one grasping member is configured to actuate translation of the first tubular member and the second tubular member.

12. The modular surgical instrument of claim 11, wherein the elongated first member is configured to translate within a portion of the first tubular member based on a position of the first tubular member with respect to the second tubular member.

13. The modular surgical instrument of claim 11, wherein an end of the second tubular member comprises interlocking portions each configured to interlock with a portion of a head assembly.

14. The modular surgical instrument of claim 13, wherein as the second tubular member translates over a portion of the first tubular member, an end of the second tubular member is configured to compress the end of the first tubular member.

15. The modular surgical instrument of claim 11, wherein in an open position, the elongated first member and first tubular member are configured to translate through the second tubular member in unison.

16. The modular surgical instrument of claim 11, wherein in a locked position, the elongated first member is configured to translate through the second tubular member independent of the first tubular member.

17. The modular surgical instrument of claim 11, wherein a second working end is configured to be removable coupled to the first end of the elongated second member.

18. The modular surgical instrument of claim 17, wherein the second working end comprises:
a third interlocking portion disposed on a proximal end of the second working end and configured to interlock with the second interlocking portion of the working end attachment,
a third tubular member configured to house the portion of the elongated first member, and
a fourth tubular member configured to house the portion of the elongated first member and a portion of the third tubular member.

19. A surgical system comprising:
an implant comprising an assembly head and a fastener, the assembly head comprising a crown configured to be positioned on a head of the fastener and at least one expandable retainer formed as an open ring and configured to lock the assembly head onto the fastener; and
a surgical instrument comprising: an elongated first member;
a first tubular member, a portion of the elongated first member being positioned within the first tubular member;
a second tubular member, the portion of the elongated first member and a portion of the first tubular member being positioned within the second tubular member; and
at least one grasping member,
wherein a portion of the at least one grasping member is pivotably coupled to the first tubular member and another portion of the at least one grasping member is pivotably coupled to the second tubular member,
wherein the at least one grasping member is configured to actuate translation of the first tubular member and the second tubular member,
wherein a distal end of the first tubular member is configured to interlock the assembly head onto the fastener by contacting an upper surface of the crown and forcing the crown into a receiving portion of the assembly head.

20. The surgical system of claim 19, wherein the at least one grasping member is configured to actuate translation of the first tubular member and the second tubular member to interlock the assembly head and the fastener.

21. The surgical system of claim 19, wherein the elongated first member is configured to translate within a portion of the first tubular member based on a position of the first tubular member with respect to the second tubular member.

22. The surgical system of claim 19, wherein, to lock the assembly head onto the fastener, the at least one expandable retainer is positioned between the crown of the assembly head and an inner surface of the receiving portion of the assembly head.

* * * * *